United States Patent [19]

Sasaki

[11] Patent Number: 4,751,926
[45] Date of Patent: Jun. 21, 1988

[54] INSTRUMENT FOR SUBCUTANEOUS INSERTION OF AN INJECTION RESERVOIR

[75] Inventor: Gordon H. Sasaki, Pasadena, Calif.

[73] Assignee: Dow Corning Wright Corporation, Arlington, Tenn.

[21] Appl. No.: 907,204

[22] Filed: Sep. 12, 1986

[51] Int. Cl.[4] ............................................. A61B 17/00
[52] U.S. Cl. .................. 128/303 R; 128/330; 604/57
[58] Field of Search .............. 128/303 R, 330, 341, 128/361; 123/7, 8; 604/57, 59, 60

[56] References Cited

U.S. PATENT DOCUMENTS

| | | | |
|---|---|---|---|
| 829,409 | 8/1906 | Manning | 128/341 |
| 3,416,713 | 12/1968 | Stephens | 223/104 |
| 4,214,585 | 7/1980 | Bailey, Jr. | 128/303 R |

Primary Examiner—Dalton L. Truluck
Assistant Examiner—Denise Whelton
Attorney, Agent, or Firm—Susan M. Cornwall

[57] ABSTRACT

An instrument for subcutaneously inserting an injection reservoir attached to an inflatable prosthesis by means of an elongated fluid conduit is disclosed. The instrument has a hollowed end which holds the injection reservoir to be inserted in a mating, releasable fashion and that end is attached to a handle for guiding the hollowed end to the desired site. Desirably, but optionally, the end of the handle of the instrument is provided with a shaped tapered portion to act as a dilator to create a subcutaneous pocket prior to insertion of the injection reservoir.

5 Claims, 1 Drawing Sheet

INSTRUMENT FOR SUBCUTANEOUS INSERTION OF AN INJECTION RESERVOIR

BACKGROUND OF THE INVENTION

This invention relates to a surgical instrument for the subcutaneous insertion and removal of an injection reservoir used for the inflation of an implantable prosthesis such as a tissue expander.

Inflatable prostheses such as mammary prostheses and tissue expanders can be inflated subcutaneously by two commonly available means. The first means is via a resealable valve mounted directly on the surface of the prosthesis itself to permit introduction of a fluid into the prosthesis via a hypodermic syringe. The second means for inflating such a prosthesis is via an injection reservoir which is not itself expandable and has a self-sealing area designed to be punctured by a hypodermic needle to permit introduction of a fluid into the hollow center of the injection reservoir which then travels through an elongated fluid conduit such as a piece of tubing over to the inflatable prosthesis itself. Remotely placed injection reservoirs of the second type have also been referred to as "remote valves", "subcutaneous injection sites", "valve domes" and "puncture housings"; the term "injection reservoir" shall be used herein to designate such inflation means. Each type of inflation means has its own advantages and disadvantages.

An implant such as a tissue expander with a remote injection reservoir may be selected because, for example, of the ease with which the injection reservoir can be found by palpation or to reduce the possibility that the prosthesis envelope itself may be accidentally damaged during inflation by a needle puncture. To implant such a prosthesis, the surgeon must not only create a subcutaneous pocket for the prosthesis itself, but must also create a pocket for the injection reservoir and the tubing connecting it to the tissue expander.

It is preferable to minimize the number of incisions made through the skin during a surgical procedure for obvious reasons; therefore a single incision is normally desirable and is used to create a subcutaneous pocket for the inflatable envelope of the tissue expander as well as the injection reservoir. This can create some difficulty for the surgeon since the injection reservoir must generally be passed along a narrow subcutaneous tunnel not much larger than the injection reservoir itself to avoid disturbing any more tissue than is necessary. The injection reservoir may tip to one side or the other as it is pushed into place or may even flip over during the insertion procedure.

Once in place, the injection reservoir generally remains in place for a period of time numbering days to weeks and during that time a capsule is observed to form around the injection reservoir as well as the tubing and the inflatable portion of the tissue expander. The formation of this capsule is a natural response to the presence of the implanted prosthesis, but creates difficulties for the surgeon when the injection reservoir is to be removed if only one incision through the skin is to be used. People vary in the type of capsules produced and it is sometimes difficult to remove the injection reservoir without making a second incision near the injection reservoir if a thick or tight capsule has formed.

SUMMARY OF THE INVENTION

One object of the present invention is to overcome the deficiencies of the prior art by providing an instrument by which an injection reservoir for an inflatable prosthesis such as a tissue expander can be subcutaneously placed in an accurate and simple fashion with a minimum of incisions through the skin and to provide a means by which the injection reservoir can be removed from the implantation site with a minimum number of incisions. Another object of the present invention is to overcome the difficulties encountered with removal of an injection reservoir when a capsule forms around the injection reservoir.

These and other objects of the present invention are provided by a instrument which comprises an elongated member having one hollowed end which contains a recess which is matched to receive the injection reservoir to be inserted in a mating, releasable relationship to carry the injection reservoir to the desired subcutaneous site without the chance that the injection reservoir may flip over during insertion and thus have the puncturable portion of the injection reservoir facing in the wrong direction towards the body. The end carrying the injection reservoir blends in with the configuration of the injection reservoir to allow smooth introduction of the injection reservoir and the first end has a substantially pointed configuration with an edge designed to sever or push aside subcutaneous tissue and create a subcutaneous pocket for the injection reservoir of substantially the same size as the injection reservoir and through which its fluid conduit (e.g., tubing) is passed. The opposite end of the elongated member serves as a handle to guide the other end to the desired site for the injection reservoir. The instrument can also contain a channel such as a bore situated towards the rear of the injection reservoir being inserted (i.e., towards the handle) through which the tubing is passed to enable the surgeon to pass the tubing into the pocket for the injection reservoir and, also to use as a guide when the injection reservoir is to be removed.

In an alternative embodiment, the handle of the instrument includes a shaped end that is used to prepare a subcutaneous pocket for the the injection reservoir.

BRIEF DESCRIPTION OF THE DRAWINGS

The above and other objects, features, and advantages of the present invention will become apparent to those skilled in the art upon an examination of the following description and drawings which are illustrative of the present invention.

In the Drawings.

DETAILED DESCRIPTION OF THE INVENTION

Figure 1:
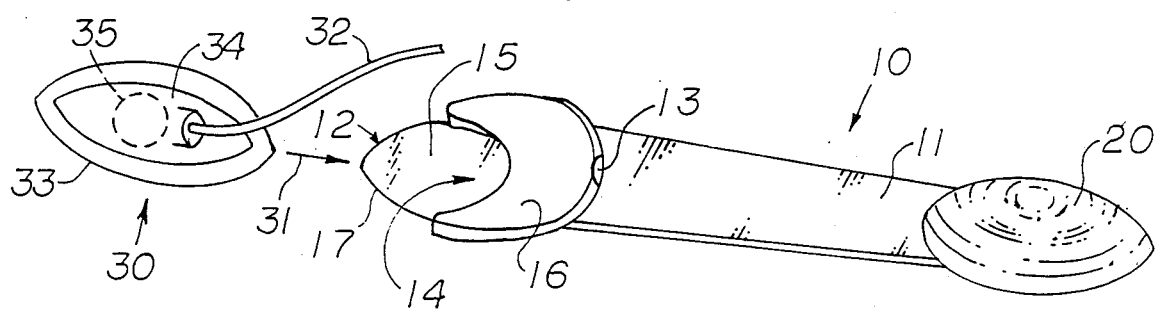
FIG. 1 is a perspective view of one embodiment of the present invention shown as instrument 10 having a handle with optional elongated portion 20 along with injection reservoir 30.
Figure 2:
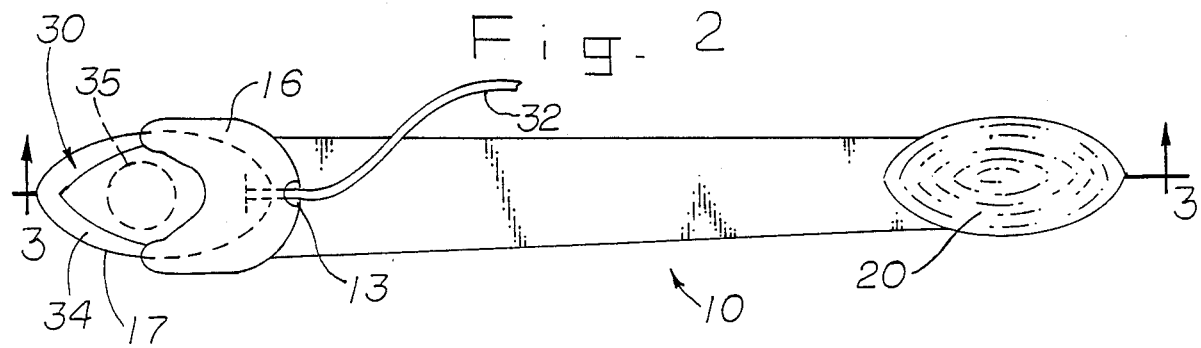
FIG. 2 is a plan view of instrument 10 showing injection reservoir 30 inserted therein.
Figure 3:
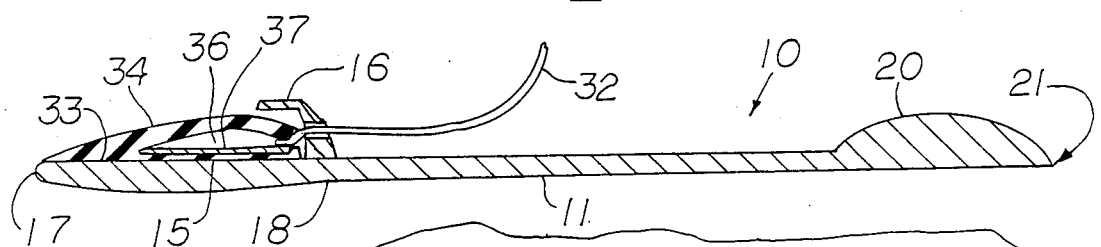
FIG. 3 is a cross-sectional view of FIG. 2 taken along section lines 3—3.

Referring to the Drawings, FIGS. 1-3 show the instrument 10 of the present invention which is an elongated member 11 having hollowed end 12 which receives injection reservoir 30 in a mating, releasable fashion when the fluid conduit of injection reservoir 30 shown as hollow tubing 32 is passed through bore 13.

The surgeon may grasp tubing 32 after it is passed through bore 13 to retain injection reservoir 30 within hollowed end 12. End 12 is configured relative to the injection reservoir to be inserted to achieve a mating relationship and thus, end 12 contains recess 14 to receive the corresponding rear portion of injection reservoir 30 and has a flat surface 15 on which the flat bottom surface 33 of injection reservoir 30 rests.

FIG. 2 shows, in outline form, the manner in which injection reservoir 30 fits within recess 14. FIG. 3 better illustrates the manner in which cover 16 which forms recess 14 is configured to blend in with the design of upper surface 34 of injection reservoir 30 which contains region 35 which is the resealable portion of surface 34 that is intended to be pierced by a hypodermic needle. End 12 is of an overall elongated shape which is substantially tapered to an edge 17 which extends around at least the front portion of end 12 which edge is shaped to permit end 12 to push aside and possibly sever tissue ahead of end 12 when it is inserted subcutaneously to thereby create a pocket for the injection reservoir 30 being inserted. It is not desirable to have edge 17 highly beveled to a sharp edge since this may result in excessive bleeding and could even result in damage to subcutaneous bodily structures or organs.

Instrument 10 as shown further contains an optional elongated portion 20 which is opposite end 12 and serves the two-fold purpose of acting as a handle by which the surgeon can guide end 12 with its injection reservoir 30 into the desired subcutaneous site and can be used as a dilator to create a subcutaneous pocket for the injection reservoir before it is actually inserted beneath the patient's tissue using end 12. To this end, elongated portion 20 has substantially the same general configuration as end 12 when the injection reservoir 30 is placed in recess 14 although portion 20 may be more flattened in configuration to ease insertion of portion 20. Portion 20 has a generally tapered edge 21 similar to edge 17 of end 12 to assist in pushing aside tissue as a pocket for the injection reservoir 30 is made.

The channel present in instrument 10 shown as bore 13 is also optional since cover 16 can be configured to have a space where the tubing passes over end 12 or else cover 16 can simply grasp the portion of injection reservoir 30 lying below the region where the tubing exits from injection reservoir 30. The presence of bore 13 does permit the surgeon to use the tubing to hold the injection reservoir in place on end 12 until he desires to release it when the desired subcutaneous site is reached and can serve as a guide for removal of the reservoir. The term "channel" as used herein includes a bore as shown or a depression in which the fluid conduit or tubing of the injection reservoir is designed to rest.

Instrument 10 is shown as having a flat lower surface 18 (rounded beneath end 12) although it could also be slightly rounded and have a beveled edge along its entire length. Similarly, member 11 could be curved to assist the surgeon in passing instrument 10 through an incision. Instrument 10 could be made of any biocompatible metal such as stainless steel or plastic such as polysulfone of the type commonly employed for surgical instruments as long as the material employed will hold its shape for the purposes described herein. A somewhat flexible material may be desirable to permit ease of insertion. The exact nature of the material used to produce instrument 10 forms no part of the present invention.

Figure 4:
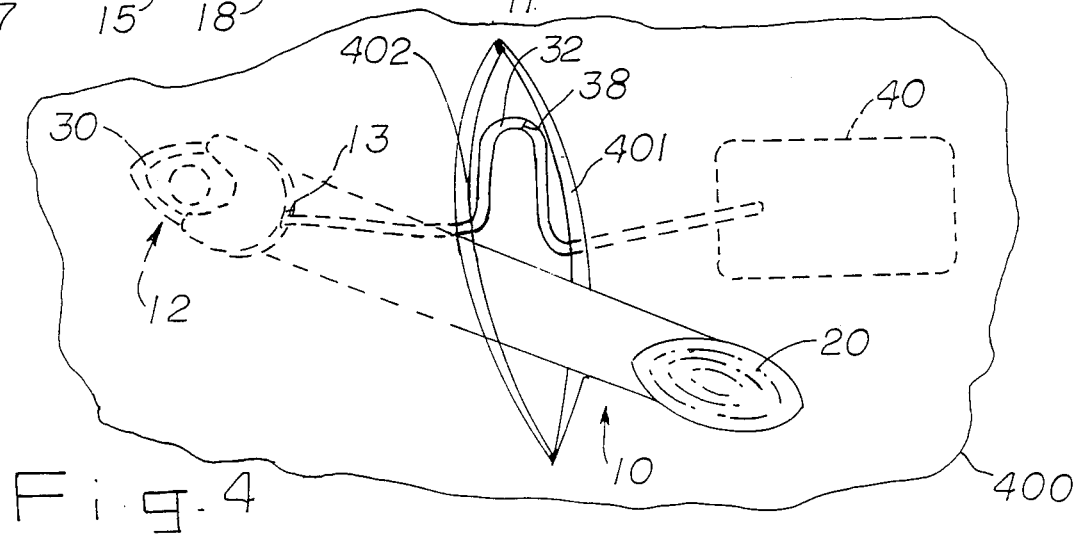
FIG. 4 illustrates the use of instrument 10 to insert injection reservoir 30 subcutaneously.

FIG. 3 shows more of the detail of the injection reservoir 30 which is a hollow dome of a medical grade material such as a silicone elastomer and contains a hollow interior region 36 which is reached by passing a hypodermic needle (not shown) through resealable region 35 up to metal needlestop 37. Tubing 32 is sealingly connected to injection reservoir 30 by means of a removable connector or is cemented in place to provide the center of tubing 32 with access to region 36. Tubing 32 then extends to, for example, an inflatable tissue expander prosthesis 40 as shown in FIG. 4 and is attached to that prosthesis in a sealing fashion. If bore 13 is employed, then it is desirable that tubing 32 be capable of being passed through bore 13, so it must be disconnectable at some point along its length. Various connector means are known to those skilled in the art. Injection reservoir 30 is merely illustrative of one type of such a reservoir that may be used. Others such as those taught in U.S. Pat. Nos. 3,971,376 to Wichterle; 4,190,040 to Schulte, and 4,543,088 to Bootman, et al. and rectangular, oblong injection reservoirs sold by, for example, McGhan Medical Corporation of Santa Barbara, Calif. with its Style 20 Round/Style 22 Rectangle McGhan Tissue Expanders (Data Sheet No. M005 1/85) can also be employed.

Having described the instrument of the present invention, the manner in which it is used will now be described with reference to FIG. 4. Using instrument 10 and injection reservoir 30 for illustrative purposes, the operative site 400 is selected by the surgeon and an incision is made in accordance with well-known surgical techniques. A subcutaneous pocket is made and the prosthesis, in this case tissue expander 40, is inserted into that pocket beneath side 401 of the incision in the patient's skin in the usual manner of inserting such prostheses. Portion 20 of instrument 10 can be used to create a subcutaneous tunnel for injection reservoir 30 by inserting portion 20 beneath side 402 of the incision in the patient's skin using end 12 as a handle or else a Hegar dilator or other surgical dilator can be used to form such a tunnel.

Injection reservoir 30 is placed on end 12 and tubing 32 is passed through bore 13 by disconnecting it from the remainder of the tubing by means of in-line connector 38 and thereafter reconnecting it to the open end of the tubing. The surgeon then passes end 12 of instrument 10 holding the tubing against member 11 to prevent injection reservoir 30 from slipping out of recess 14 and, using portion 20 as a handle, inserts injection reservoir 30 subcutaneously until the desired site for the injection reservoir 30 is reached. The surgeon releases his grasp on tubing 32 and holds injection reservoir 30 in place by pressing on the tissue overlying injection reservoir 30 while instrument 10 is withdrawn to leave the injection reservoir 30 in its desired location. It is also possible to use end 12 of instrument 10 to create a tunnel with the injection reservoir mounted in place so that the tunnel can be formed and the injection reservoir 30 placed subcutaneously in one operation by moving end 12 from side-to-side as end 12 is advanced. After injection reservoir 30 is in place, tubing 32 is removed from bore 13, the remaining tubing 32 is placed subcutaneously and the incision is closed in the usual manner.

To remove the reservoir, an incision is made and tubing 32 is passed through bore 13 and is used as a guide for end 12 until injection reservoir 30 is reached. Edge 17 is used to push aside or Cut through any capsule that may have formed until injection reservoir 30 is received within end 12. The surgeon grips the tubing and removes end 12 along with injection reservoir 30. Bore 13 need not be used since end 12 can simply be inserted using tubing 32 as a guide until injection reservoir 30 is reached.

Other modifications of the instrument of the present invention will become apparent to those skilled in the art from an examination of the above specification and drawings. Therefore, other variations of the present invention may be made which fall within the scope of the following claims even though such variations were not specifically discussed above.

That which is claimed is:

1. An instrument for the subcutaneous placement of a self-sealing injection reservoir having a rear portion and a hollow interior which communicates with the interior of an implantable, inflatable prosthesis by means of an elongated fluid conduit, said instrument comprising an elongaed member having a first hollowed end having a recess dimensioned to matingly receive the rear portion of the injection reservoir in a releasable relationship, a cover on said first end which forms part of the recess, said cover positioned to fit over at least a part of the rear portion of the injection reservoir when the injection reservoir is received in the recess, and an opposite second end which serves as a handle means for guiding the first end subcutaneously into the body, said first end being of an elongated, substantially tapered configuration with an edge shaped to permit the first end to push aside tissue ahead of the first end when it is inserted subcutaneously and thereby carry the reservoir to the desired subcutaneous site, said first end dimensioned to blend in with the surface of the reservoir to permit the first end along with the reservoir to be smoothly inserted subcutaneously into the body.

2. The instrument as claimed in claim 1 wherein said first end further contains a channel through which said fluid conduit is passed before the instrument carrying the reservoir is inserted subcutaneously, said channel being placed on the first end at the rear of the reservoir being inserted such that the channel is at the rear of the first end facing the handle.

3. An instrument as claimed in claim 2 wherein the channel is a bore.

4. An instrument as claimed in claim 1 wherein said recess has a flat bottom surface on which the injection reservoir is to rest.

5. An instrument as claimed in claim 1 wherein said second end has a tapered edge to push aside subcutaneous tissue.

* * * * *